United States Patent [19]

Hanka et al.

[11] 4,169,888

[45] Oct. 2, 1979

[54] COMPOSITION OF MATTER AND PROCESS

[75] Inventors: Ladislav J. Hanka; David G. Martin, both of Kalamazoo, Mich.

[73] Assignee: The Upjohn Company, Kalamazoo, Mich.

[21] Appl. No.: 842,914

[22] Filed: Oct. 17, 1977

[51] Int. Cl.² ................. C12D 9/14; C07G 11/00
[52] U.S. Cl. .................... 424/121; 195/80 R; 435/128; 435/886
[58] Field of Search .............. 195/80 R; 424/121, 123

[56] References Cited

U.S. PATENT DOCUMENTS

| | | | |
|---|---|---|---|
| 3,655,879 | 4/1972 | Nakazawa et al. | 424/121 |
| 3,819,834 | 6/1974 | Umezawa et al. | 195/80 |

*Primary Examiner*—Alvin E. Tanenholtz
*Attorney, Agent, or Firm*—Roman Saliwanchik

[57] ABSTRACT

Novel antibiotic CC-1065 producible in a fermentation under controlled conditions using the new microorganism *Streptomyces zelensis*, NRRL 11,183. This antibiotic is active against Gram-positive bacteria, for example, *Staphylococcus aureus, Bacillus subtilis, Streptococcus pyogenes, Sarcina lutea,* and *Streptococcus faecalis.* It is also active against Gram-negative bacteria, for example, *Escherichia coli, Proteus vulgaris, Pseudomonas aeruginosa, Klebsiella pneumoniae,* and *Salmonella pullorum.* Thus, antibiotic CC-1065 can be used in various environments to eradicate or control such bacteria.

5 Claims, 3 Drawing Figures

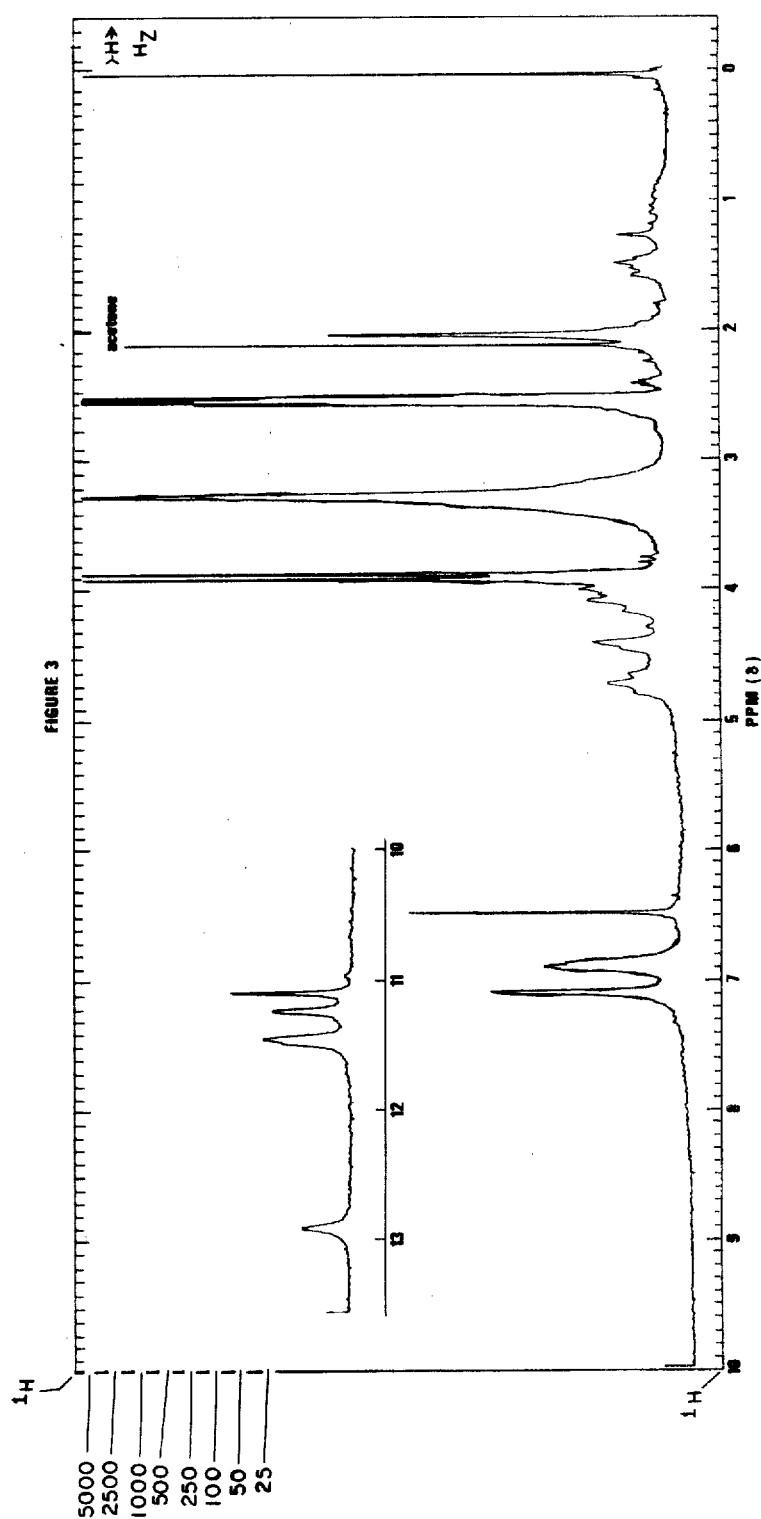

COMPOSITION OF MATTER AND PROCESS

The invention described herein was made in the course of, or under Contract NO1-CM-43753 with the National Cancer Institute, National Institutes of Health, Bethesda, Maryland 20014.

BRIEF SUMMARY OF THE INVENTION

Antibiotic CC-1065 is producible in a fermentation under controlled conditions using a biologically pure culture of the new microorganism *Streptomyces zelensis*, NRRL 11,183.

Antibiotic CC-1065 is active against various Gram-positive and Gram-negative bacteria. For example, antibiotic CC-1065 is active against *Proteus vulgaris*, and, thus, it can be used as an oil preservative to inhibit this bacterium which is known to cause spoilage in oil. Also, it is useful in washing solutions for sanitation purposes. Since antibiotic CC-1065 is active against *Bacillus subtilis*, it can be used for treating breeding places of silkworms to prevent or minimize infections which are well-known to be caused by this bacterium.

DETAILED DESCRIPTION OF THE INVENTION

Chemical and Physical Properties of Antibiotic CC-1065:

Molecular Weight: Approximately 700.

Elemental Analysis: Found: C, 61.06; H, 4.92; N, 13.17.

Ultraviolet Absorption Spectrum: A solution of antibiotic CC-1065 in dioxane displayed strong end absorption with shoulders at 230 nm (absorptivity a=68.00) and 258 nm (a=51.10) and a maximum at 364 nm (a=66.10).

Figure 1:
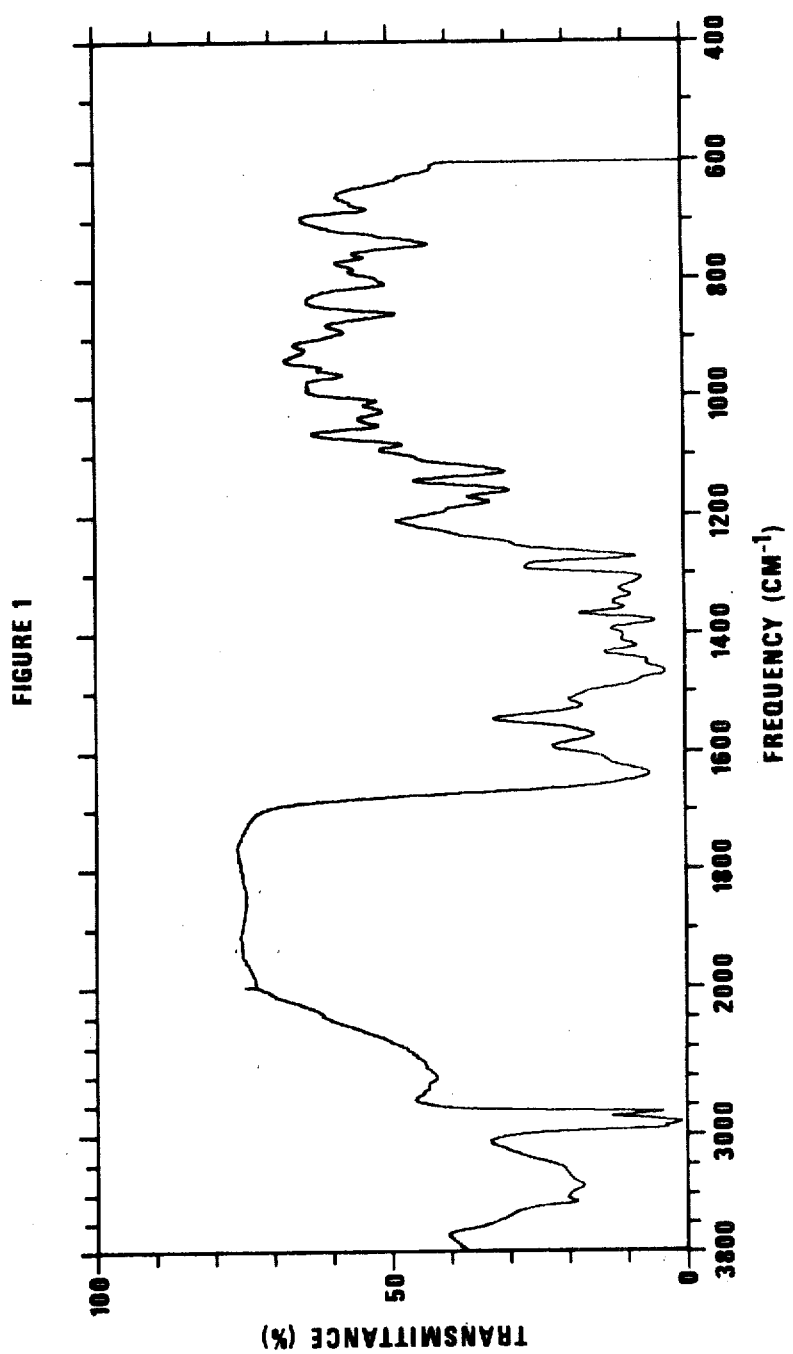

Infrared Absorption Spectrum:

Antibiotic CC-1065 has a characteristic infrared absorption spectrum in a mineral oil mull in the range of 3800–600 wave numbers (cm$^{-1}$) as shown in FIG. 1 of the drawings. The spectrum was obtained using a Digilab Model 14 D Fourier transform spectrophotometer.

Peaks are observed at the following wave lengths expressed in reciprocal centimeters. Peaks at 2960, 2920, 2850, 1465 and 1377 cm$^{-1}$ are due in part to the aliphatic C-H vibrations of mineral oil.

| Band Frequency (Wave Numbers) | Intensity |
|---|---|
| 3460 | S |
| 3350 | S |
| 3230 | S, sh |
| 2960 | S |
| 2920 | S |
| 2850 | S |
| 2610 | M |
| 1635 | S |
| 1610 | S, sh |
| 1570 | S |
| 1520 | S |
| 1480 | S, sh |
| 1465 | S |
| 1445 | S |
| 1420 | S |
| 1403 | S |
| 1377 | S |
| 1354 | S |
| 1333 | S |
| 1304 | S |
| 1268 | S |
| 1243 | M, sh |
| 1187 | M |
| 1175 | M |
| 1156 | M |
| 1125 | M |
| 1100 | M, sh |
| 1078 | M |
| 1047 | M |
| 1023 | M |
| 1005 | M |
| 962 | W |
| 948 | W |
| 918 | W |
| 888 | W |
| 856 | M |
| 805 | M |
| 779 | W |
| 760 | W |
| 737 | M |
| 678 | W |

Key:
S = Strong
M = Medium
W = Weak
sh = shoulder

Solubilities: Antibiotic CC-1065 is soluble in solvents such as dimethylsulfoxide (DMSO), dimethylformamide, acetone, methylene chloride, ethyl acetate, dioxane, and chloroform.

Figure 2:
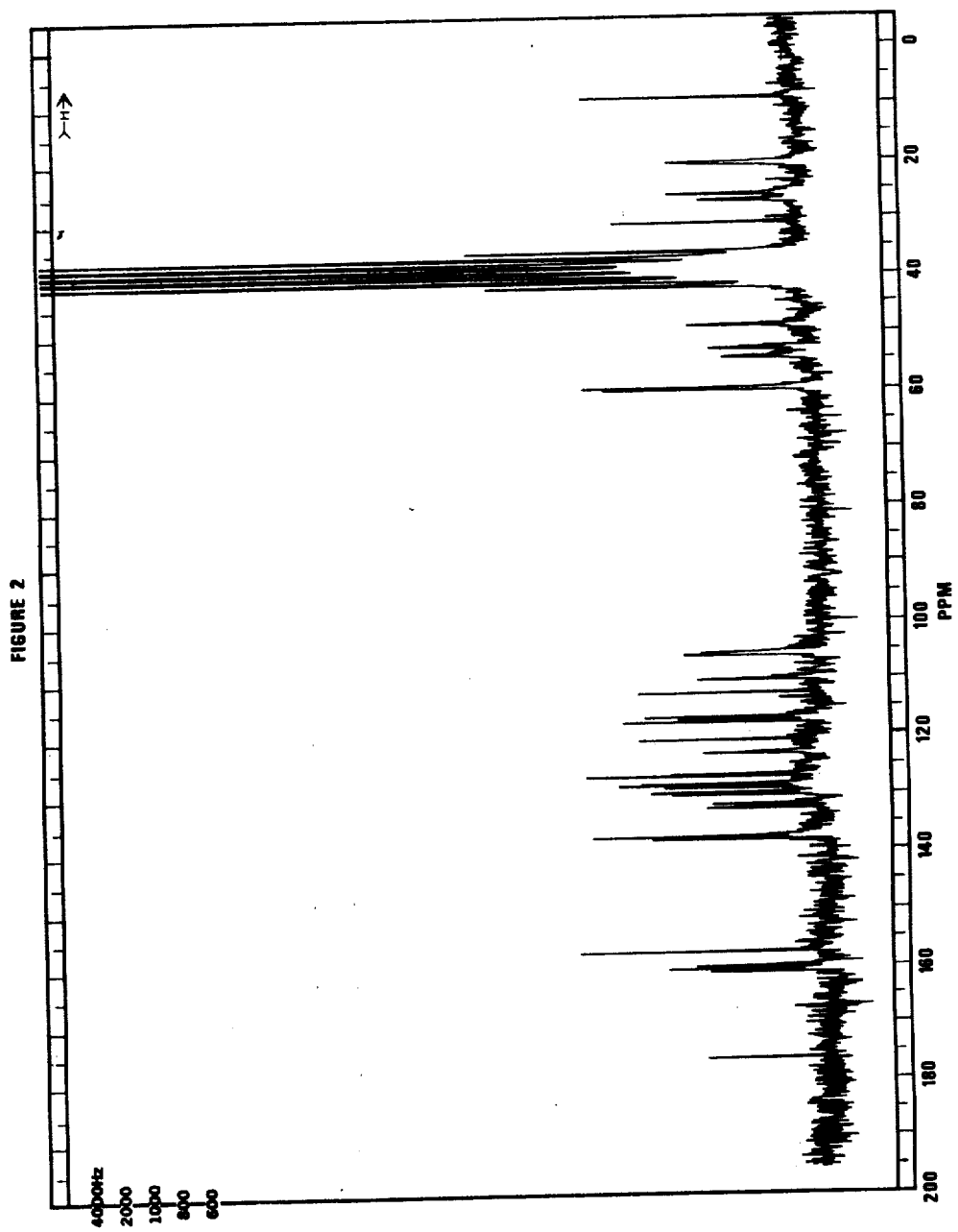

$^{13}$C-Nuclear Magnetic Resonance (NMR) Spectrum: The $^{13}$C-NMR spectrum of antibiotic CC-1065 at 20 MHZ is shown in FIG. 2 of the drawings. The $^{13}$C-NMR spectrum was observed on a Varian CFT-20 Spectrometer on a solution (ca. 1.0 ml, ca. 75 mg/ml) of the sample of antibiotic CC-1065 in deutero dimethylsulfoxide (d 6 DMSO). The spectrum was calibrated against the center line of d 6 DMSO assigned as 39.6 p.p.m. relative to tetramethylsilane as 0 p.p.m. Frequencies were recorded in p.p.m. downfield from tetramethylsilane.

Proton Magnetic Resonance ('H-NMR) Spectrum: The 'H-NMR spectrum of antibiotic CC-1065 at 100 MHZ is shown in FIG. 3 of the drawings. The 'H-NMR spectrum was observed on a Varian XL-100-15 Spectrometer on a solution (ca. 0.5 ml, ca. 150 mg/ml) of the sample of antibiotic CC-1065 in deutero dimethylsulfoxide (d 6 DMSO). The spectrum was calibrated against internal tetramethylsilane and frequencies were recorded in p.p.m. downfield from tetramethylsilane.

Antibacterial Spectrum Of Antibiotic CC-1065: Antimicrobial CC-1065 is active against various Gram-positive and Gram-negative bacteria and fungi as shown in the following table. The procedures for the tests are as follows:

The MIC were determined by standard bactercidal methods using two-fold dilutions of the antibiotic in Brain Heart Infusion Broth (Difco Lab., Detroit, Michigan). The inocula are overnight cultures of the test organisms, diluted so that the final population contains approximately $10^5$ cells/ml. The tubes are incubated at 28°–37° C. for 42 hours. The MIC is determined by transferring 0.1 ml. of broth from 42 hour tubes showing no growth into 10 ml of antibiotic free broth; tubes with no growth in 24 hours are considered to have contained bactercidal concentrations. An excellent broth for the fungi contains: $KH_2PO_4$, 0.5%; dextrose, 3.0%; yeast extract, 0.7%.

| Microorganism | Minimum Inhibitory Concentration (mcg/ml) |
|---|---|
| Gram-Positive Bacteria: | |
| Staphylococcus aureus UC 76 | 0.0015 |
| Staphylococcus aureus UC 552 | 0.003 |
| Staphylococcus aureus UC 70 | 0.0015 |
| Staphylococcus aureus UC 3665 | 0.003 |
| Bacillus subtilis UC 564 | 0.025 |
| Streptococcus pyogenes UC 6055 | 0.0008 |
| Sarcina lutea UC 130 | 0.012 |
| Streptococcus faecalis UC 157 | 0.012 |
| Streptococcus faecalis UC 3235 | 0.003 |
| Gram-Negative Bacteria: | |
| Escherichia coli UC 51 | 0.32 |
| Proteus vulgaris UC 93 | 0.08 |
| Pseudomonas aeruginosa UC 95 | 0.08 |
| Pseudomonas mildenbergii UC 3029 | 0.3 |
| Salmonella gallinarum UC 265 | 2.5 |
| Klebsiella pneumoniae UC 57 | 0.08 |
| Salmonella schottmuelleri UC 126 | 0.3 |
| Salmonella pullorum UC 267 | 0.08 |
| Fungi: | |
| Candida albicans UC 1392 | 0.3 |
| Saccharomyces cerevisiae UC 1337 | 0.04 |
| Saccharomyces pastorianus UC 1342 | 0.3 |
| Penicillium oxalicum UC 1268 | 0.02 |

"U" is a registered trademark of The Upjohn Company Culture Collection. These cultures can be obtained from The Upjohn Company in Kalamazoo, Michigan, upon request.

THE MICROORGANISM

The microorganism used for the production of antibiotic CC-1065 is *Streptomyces zelensis*, NRRL 11,183.

A subculture of this microorganism can be obtained from the permanent collection of the Northern Regional Research Laboratory, U.S. Department of Agriculture, Peoria, Illinois, U.S.A. Its accession number in this depository is NRRL 11,183. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

A new soil isolate, which produces antibiotic CC-1065, is characterized and considered to be a new species of the genus Streptomyces on the basis of its conformity to the general characteristics of the genus [Pridham, T. G., and H. D. Tresner. 1974. Part 17. Actinomycetes and related organisms. Family VII. Streptomycetaceae Waksman and Henrici 1943. Genus I. Streptomyces. p. 748. In: Bergey's Manual of Determinative Bacteriology 8th ed. Buchanan and Gibbons (eds.). The Williams and Wilkins Co., Baltimore.].

This new isolate has gray-green aerial growth, is melanin negative, has short, straight to open spiral to spiral spore chains of round spores with a spiny or thorny surface.

The subject culture can be differentiated from most members of the limited "green" group (Green group cultures are those in the Viridis Series of Waksman [Waksman, S. A. 1961. The actinomycetes, Vol. 2, Classification, identification, and descriptions of genera and species. The Williams and Wilkins Co., Baltimore.] and Baldacci [Baldacci, E. 1958. Development in the classification of actinomycetes. Giornale di Microbiologia. 6:10-27.]; the *prasinus* color group of Ettlinger, et al. [Ettlinger, L., R. Corbaz und R. Hütter. 1958. Zur Sytematik der Actinomyceten. 4. Eine Arteinteilung der Gattung Streptomyces Waksman et Henrici. Archiv. für Mikrobiologie. 31:326-358.]; the prasinus odor azureus-glaucus group of Hütter [Hütter, R. 1967. Systematik der Streptomyceten unter besondere Berucksictigung der von ihnen gebildeten Antibiotica. S. Karger, Basel.]; the *malachiticus* group of Küster [Küster, E. 1970. Note on the taxonomy and ecology of *Streptomyces malachiticus* and related species. International Journal of Systematic Bacteriology. 20:25-29.]; the greenspore color group X of Kutzner [Kutzner, H. J. 1956. Beitrag zur Systematic und Okologie der Gattung Streptomyces Waksm. et Henrici. Diss. Landw. Hocksch. Hokenhein.]; the prasinomycin-producers of Myers, et al. [Myers, E., G. J. Miraglia, D. A. Smith, H. I. Basch, F. E. Pansy, W. H. Trejo, and R. Donovick. 1968. Biological characterization of prasinomycin, a phosphorus-containing antibiotic. Appl. Microbiol. 16:603-608] [Myers, E., R. Donovick, F. L. Weisenborn, and F. E. Pansy. 1970. Prasinomycin. U.S. Pat. No. 3,493,653.]; those in Tables 11 and 12 in Küster [Küster, E. 1972. Simple Working Key for the classification and identification of named taxa included in the International Streptomyces Project. Int. J. Syst. Bacteriol. 22:139-148.]; and those in the green series of Pridham and Tresner [Pridham, T. G., and H. D. Tresner, 1974. Part 17. Actinomycetes and related organisms. Family VII. Streptomycetaceae Waksman and Henrici 1943. Genus I. Streptomyces. Table 17.46 a–d Green Series. p. 825. In: Bergey's Manual of Determinative Bacteriology 8th ed. Buchanan and Gibbons (eds.). The Williams and Wilkins Co., Baltimore.]) of Streptomyces by the production of antibiotic CC-1065, by its growth at 4°-45° C. and by its distinctive spore chains and spores. It also can be distinguished from a more recently characterized culture, *Streptomyces espinosus* [Argoudelis, A. D., et al. 1972. Lincomycin production. U.S. Pat. No. 3,697,380 Oct.] [Reusser, F. and A. D. Argoudelis. 1974. Process for preparing lincomycin. U.S. Pat. No. 3,833,475 Sept.] by its color pattern on Ektachrome, its carbon utilization pattern, its growth at 4°-45° C. and its production of antibiotic CC-1065.

Therefore, it is proposed that the new soil isolate be designated *Streptomyces zelensis* (derived from zeleny=-green in Czech.) Dietz and Li sp.n. and that this type species be designated the type subspecies *Streptomyces zelensis* subsp. *zelensis* in accordance with the rules set forth in the International Code of Nomenclature of Bacterial [Lapage, S. P., et al., (eds.). 1976 Revision. International Code of Nomenclature of Bacteria. Amer. Soc. for Microbiol., Wash. D.C. 180 pp.].

Taxonomy: *Streptomyces zelensis* Dietz. and Li sp.n.

Color characteristics: Aerial growth green-gray or gray-green. Melanin negative. The appearance of the culture on Ektachrome is given in Table 1. Reference color characteristics are given in Table 2. The culture may be placed in the yellow (Y) and green (GN) color series of Tresner and Backus [Tresner, H. D., and E. J. Backus. 1963. System of color wheels for streptomycete taxonomy. Applied Microbiol. 11:335-338].

Microscopic characteristics: Spore chains at first straight, then becoming open spiral to spiral (RF, RA, S) in the sense of Pridham, et. al. [Pridham, T. G., C. W. Hesseltine, and R. G. Benedict. 1958. A guide for the classification of streptomycetes according to selected groups. Placement of strains in morphological sections.

Applied Microbiol. 6:52-79.]. Spore surface spiny or thorny.

Cultural and biochemical characteristics: Cultural and biochemical characteristics are described in Table 3.

Carbon utilization: Growth on carbon compounds was determined using the procedures of Pridham and Gottlieb [Pridham, T. G., and D. Gottlieb. 1948. The utilization of carbon compounds by some Actinomycetales as an aid for species determination. J. Bacteriol. 56:107-114.] and Shirling and Gottlieb [Shirling, E. B., and D. Gottlieb. 1966. Methods for characterization of Streptomyces species. International Journal of Systematic Bacteriology 16:313-340.]. In the former the culture grew well on D-xylose, D-fructose, D-galactose, D-glucose, D-mannose, maltose, cellobiose, dextrin, soluble starch, glycerol, D-mannitol, and inositol; moderately on L-arabinose, sodium oxalate, sodium acetate, and sodium succinate; and poorly on rhamnose, sucrose, lactose, raffinose, inulin, dulcitol, D-sorbitol, salicin, phenol, sodium formate, sodium tartrate, sodium salicylate, sodium citrate, and the control (no carbon compound added). The culture did not grow on cresol. In the latter the culture grew well on the positive control (D-glucose), D-xylose, inositol, D-mannitol, and D-fructose; moderately on L-arabinose; and poorly on the negative control (basal medium). It did not grow on sucrose, rhamnose, raffinose, or cellulose.

Temperature: The culture grew slightly at 4° C., moderately at 18°, 24°, and 45° C., and well at 28°, 32°, and 37° C. There was no growth at 55° C. Media used for temperature studies were Bennett's, Czapek's sucrose, maltose-tryptone, and Hickey-Tresner agars.

Antibiotic-producing properties: The culture produces antibiotic CC-1065.

Table 1

| Appearance of *Streptomyces zelensis* on Ektachrome | | |
|---|---|---|
| Agar Medium | Surface | Reverse |
| Bennett's | Trace gray | Yellow-tan |
| Czapek's sucrose | Pale gray | Colorless |
| Maltose-tryptone | Gray-green | Tan |
| Peptone-iron | Gray-white | Tan |
| 0.1% Tyrosine | Trace gray | Pale yellow-tan |
| Casein starch | Pale gray-green | Pale tan |

Table 2

| | Reference Color Characteristics of *Streptomyces zelensis* | | |
|---|---|---|---|
| | | ISCC-NBS Centroid Color Charts Standard Sample No. 2106 [Supplement to NBS Circular 553*] | |
| Agar Medium | Determination | Color chip | Color name |
| Bennett's | S | 121 p. YG | Pale yellow green |
| | R | 86 l. Y | Light yellow |
| | P | 76 l. yBr | Light yellowish brown |
| Czapek's source | S | 121 l. YG | Pale yellow green |
| | R | 92 y. White | Yellowish white |
| | P | — | — |
| Maltose-tryptone | S | 122 gy. YG | Grayish yellow green |
| | R | 91 d. gy. Y | Dark grayish yellow |
| | P | 76 l. yBr | Light yellowish brown |
| Hickey-Tresner | S | 122 gy. YG | Grayish yellow green |
| | R | 90 gy. Y | Grayish yellow |
| | P | 76 l. yBr | Light yellowish brown |
| Yeast extract- malt extract (ISP-2) | S | 122 gy. YG | Grayish yellow green |
| | R | 91 d. gy. Y | Dark grayish yellow |
| | P | 77 m. yBr | Moderate yellowish brown |
| Oatmeal (ISP-3) | S | 121 p. YG | Pale yellow green |
| | R | 104 p. gy. Y | Pale grayish yellow |
| | P | — | — |
| Inorganic-salts starch (ISP-4) | S | 122 gy. YG | Grayish yellow green |
| | R | 105 gy. gY | Grayish greenish yellow |
| | P | 76 l. yBr | Light yellowish brown |
| Glycerol-asparagine (ISP-5) | S | 121 p. YG | Pale yellow green |
| | R | 90 gy. Y | Grayish yellow |
| | P | — | — |

S = Surface
R = Reverse
P = Pigment
*Kelly, K.L., and D.B. Judd. 1955. The ISCC-NBS method of designating colors and a dictionary of color names. U.S. Dept. Comm. Circ. 553.

Table 3

| Cultural and Biochemical Characteristics of *Streptomyces zelensis* | | | |
|---|---|---|---|
| Medium | Surface | Reverse | Other characteristics |
| Agar Media | | | |
| Peptone-iron | Pale gray-green | Tan | Tan pigment Melanin negative |
| Calcium malate | Pale gray-green | Olive | No pigment Malate not solubilized |
| Glucose-asparagine | Pale gray-green | Pale chartreuse | No pigment |
| Skim milk | Trace pale gray-pink | Orange-tan | Orange-tan pigment Casein solubilized |
| Tyrosine | Green-gray | Brown | Light brown pigment Tyrosine solubilized |
| Xanthine | Green-gray | Light tan | Light tan pigment Xanthine not solubilized |

Table 3-continued

Cultural and Biochemical Characteristics of *Streptomyces zelensis*

| Medium | Surface | Reverse | Other characteristics |
|---|---|---|---|
| Nutrient starch | green-gray | Yellow-green-tan | Light tan<br>Starch hydrolyzed |
| Yeast extract-malt extract | Green | Tan | Tan pigment |
| Peptone-yeast extract-iron (ISP-6) | Pale gray-white | Tan | Tan pigment<br>Melanin negative |
| Tyrosine (ISP-7) | Gray-green | Gray | No pigment<br>Melanin negative |
| Gelatin Media | | | |
| Plain | White aerial growth on surface pellicle | — | Yellow-tan pigment<br>Complete liquefaction |
| Nutrient | White aerial growth on surface pellicle | — | Yellow-tan pigment<br>Complete liquefaction |
| Broth Media | | | |
| Synthetic | — | — | Very slight bottom growth<br>Nitrate reduced to nitrite |
| Nutrient | Green-white aerial growth on surface pellicle | — | Yellow to yellow-tan pigment<br>Very slight bottom growth<br>Nitrate reduced to nitrite |
| Litmus milk | Gray-green-white aerial growth on surface pellicle | — | Blue surface pigment in two of three tubes<br>Tan pigment<br>Peptonization<br>pH 7.9 |

The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conductive to satisfactory growth of the microorganism, for example, between about 18° and 40° C., and preferably between about 20° and 28° C. Ordinarily, optimum production of the compound is obtained in about 3 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by extraction with solvents such as methylene chloride, acetone, butanol, ethyl acetate and the like; and silica gel chromatography can be used to purify crude preparations of the antibiotic.

In a preferred recovery process the compound produced by the subject process is recovered from the culture medium by separation of the mycelia and undissolved solids by conventional means, such as by filtration or centrifugation and solvent extraction of both mycelial cake and clarified broth. The mycelial cake is extracted with acetone and the extract evaporated under reduced pressure to an aqueous concentrate. The aqueous concentrate is added to the filtered broth, which is then extracted three times with a half volume of methylene chloride. The combined extracts are evaporated under reduced pressure and the resulting oil is diluted with Skellysolve B (isomeric hexanes). The resulting suspension is chilled overnight after which the solids are collected, washed with Skellysolve B and dried to give a relatively crude preparation (yellow-brown solid) of antibiotic CC-1065.

The crude antibiotic preparation, obtained as described above, is subjected to purification procedures to yield an essentially pure crystalline preparation of antibiotic CC-1065. An initial purification procedure is to extract the crude preparation of antibiotic CC-1065 with acetone. Upon evaporation of the acetone, the resulting residue is triturated with methanol to yield a crystalline preparation of antibiotic CC-1065. These crystals can be washed with cold methanol to improve their purity. Further purification of the antibiotic CC-1065 preparation is achieved by chromatography on silica gel with crystallization of the active fractions.

Final purity (essentially pure preparation of antibiotic CC-1065) is achieved by recrystallization of the above antibiotic CC-1065 preparation from acetone-methanol.

The active fractions from the silica gel chromatography column, referred to above, are determined by thin layer chromatography (tlc) bioautography. In this procedure, a 1 µg antibiotic sample is spotted on Baker flex silica gel IB-F (J. T. Baker Chemical Co., Phillipsburg, N.J.) and bioautographed on *Bacillus subtilis* (synthetic medium) or *Sarcina lutea* after development in a solvent consisting of 90 parts chloroform, 10 parts methanol, and 0.5 parts concentrated ammonium hydroxide. The antibiotic CC-1065 tlc zone from 1 µg or higher levels of a crystalline sample can also be visualized with UV light (254 nm), and is visible as an amber zone in normal light.

The synthetic medium for *Bacillus subtilis*, referred to above, is as follows:

| | |
|---|---|
| $Na_2HPO_4$ | 1.7 g |
| $KH_2PO_4$ | 2.0 g |
| $(NH_4)_2SO_4$ | 1.0 g |
| $MgSO_4$ | 0.1 g |
| Glucose | 2.0 g |
| Metallic Ions | 1.0 ml |
| Agar | 15.0 g |
| Distilled $H_2O$ | 1 liter |

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces zelensis*, NRRL 11,183, is used to inoculate 500-ml Erlenmeyer seed flasks containing 100 ml of sterile medium consisting of the following ingredients:

| | |
|---|---|
| Yeast Extract* | 0.3% |
| Bacto-Tryptone* | 0.5% |
| Dextrin** | 0.1% |

*obtained from Difco Labs., Detroit, Michigan.
**obtained from A.E. Staley Mfg., Decatur, Illinois.

This seed medium is incubated at 28° C. for 48 hours on a Gump rotary shaker operating at 250 r.p.m.

Seed inoculum, prepared as described above, is used to inoculate 500-ml Erlenmeyer fermentation flasks containing 100 ml of sterile fermentation medium consisting of the following ingredients:

| | |
|---|---|
| Black Strap Molasses* | 1% |
| Dextrin | 1% |
| Bacto-Tryptone | 1% |
| $CaCO_3$ | 0.5% |
| NaCl | 0.2% |

*obtained from Knappen-Milling Co., Augusta, Michigan.

The presterilization pH is 7.2. The fermentation flasks are inoculated at the rate of 5 ml of seed inoculum per 100 ml of fermentation medium. The fermentation flasks are incubated for 120 hours at a temperature of 28° C. on a Gump rotary shaker operating at 250 r.p.m.

Assay of antibiotic CC-1065 is accomplished by extracting the whole beer with two volumes of methylene chloride. Varying quantities of the methylene chloride extract (20 µl, 10µl, 5 µl, 2 µl, 1 µl) are spotted on Polygram SIL-N-HR silica gel sheets (Macherey-Nagel and Co., Doren, Germany) and bioautographed on *Sarcina lutea* after development in a solvent system containing: methyl alcohol, 10 ml; chloroform, 90 ml; and ammonium hydroxide, 0.5 ml.

Preparation Of Agar Trays of *Sarcina lutea* UC 130 (ATCC 9341) for Bioautography 125 ml of cooled (48° C.) Penassay Seed Agar (Difco Laboratories, Detroit, Michigan) inoculated with a thawed broth culture of *S. lutea* (0.5 ml/liter) is poured into 200 mm×500 mm plastic trays and allowed to solidify. The agar trays are incubated 20-24 hours at 32° C.

The *S. lutea* inoculum, containing $10^{-9}$ cells/ml is stored as aliquots in the gaseous phase of liquid nitrogen.

B. Recovery

Fermentation broth, obtained as described above, from four 10 l tank fermentations is filtered through a pad of Celatom FW 40 (Eagle Picher's diatomaceous earth). The mycelial cake is extracted with acetone and the extract evaporated under reduced pressure to an aqueous concentrate. The aqueous concentrate is added to the clarified broth which is then extracted three times with a half volume of methylene chloride. The methylene chloride extracts are evaporated under reduced pressure to an oil, which is diluted with 1.5 l of Skellysolve B, and the resulting suspension chilled overnight. The solids are then collected, washed with Skellysolve B and dried, affording a relatively crude preparation of antibiotic CC-1065 as a yellow-brown solid. This crude preparation can be assayed by tlc bioautography as described previously.

C. Purification

A crude preparation of antibiotic CC-1065, obtained as described above, is extracted with acetone (400–800 ml) to remove small amounts of acetone insoluble materials. The acetone is evaporated, and the residue is triturated with methanol (10 ml/gm). The suspension is chilled overnight and the resulting crystalline solid collected, washed with cold methanol, and dried; yield, 40–180 mg of a crystalline preparation of antibiotic CC-1065. This crystalline preparation is assayed by tlc bioautography on silica gel as described previously.

Further purification is achieved by chromatography on silica gel and crystallization of the active fractions. For example, 470 mg of these crystalline solids are dissolved in 940 ml of acetone and evaporated onto 10 ml of silica gel (Geduran TM SI60, E. M. Laboratories, Inc., Elmsford, N.Y.). The resulting powder is chromatographed on 100 ml of silica gel eluted with a solvent consisting of 80 parts chloroform, 20 parts methanol, and 4 parts ammonium hydroxide. Twenty fractions of 20 ml each are collected and evaporated to dryness. The fractions are assayed by tlc bioautography. Fractions 6–19 are pooled and triturated with methanol affording 218 mg of high quality crystalline antibiotic CC-1065. Final purity can be achieved by recrystallization from acetone-methanol which yields 167 mg (77% recovery) of essentially pure crystals of antibiotic CC-1065.

We claim:

1. Antibiotic CC-1065 which is active against Gram-positive and Gram-negative bacteria, and which in its essentially pure form has the following characteristics:
   (a) molecular weight of approximately 700;
   (b) has the following elemental analysis: C, 61.06; H, 4.92; N, 13.17;
   (c) is soluble in dimethylsulfoxide, dimethylformamide, acetone, methylene chloride, ethyl acetate and dioxane;
   (d) has a characteristic infrared absorption spectrum when dissolved in a mineral oil mull as shown in FIG. 1 of the drawings;
   (e) has a characteristic NMR spectrum as shown in FIG. 2 of the drawings; and,
   (f) has a characteristic proton spectrum as shown in FIG. 3 of the drawings.

2. A process for preparing antibiotic CC-1065 which comprises cultivating *Streptomyces zelensis*, having the identifying characteristics of NRRL 11,183, in an aqueous nutrient medium under aerobic conditions until substantial antibiotic CC-1065 activity is imparted to said medium.

3. A process, according to claim 2, wherein said aqueous nutrient medium contains a source of assimilable carbohydrate and assimilable nitrogen.

4. A process for recovering antibiotic CC-1065 from a fermentation beer which comprises extraction of the filtered beer with a solvent for antibiotic CC-1065, and recovering antibiotic CC-1065 from said extracts.

5. A process, according to claim 4, wherein said solvent for antibiotic CC-1065 is selected from the group consisting of acetone, methylene chloride, butanol, and ethyl acetate.

* * * * *